United States Patent [19]

Bowles et al.

[11] Patent Number: 4,621,633
[45] Date of Patent: Nov. 11, 1986

[54] HEATED OXYGEN SYSTEM AND PORTABLE EQUIPMENT CASE FOR HYPOTHERMIA VICTIMS

[76] Inventors: Dale D. Bowles, 2443 Hemlock; Charles L. Parmley, 13 Iris, both of Granite City, Ill. 62040

[21] Appl. No.: 649,268

[22] Filed: Sep. 10, 1984

[51] Int. Cl.[4] ............................................. A61M 16/00
[52] U.S. Cl. ........................... 128/203.17; 128/203.27; 128/204.17
[58] Field of Search ...................... 128/203.17, 203.26, 128/203.27, 204.17, 204.26, 204.15

[56] References Cited

U.S. PATENT DOCUMENTS

| | | | |
|---|---|---|---|
| 2,166,574 | 7/1939 | Adolphsen | 128/200.13 |
| 4,014,384 | 3/1977 | Marcus | 128/204.17 |
| 4,060,576 | 11/1977 | Grant | 128/203.27 |
| 4,076,021 | 2/1978 | Thompson | 128/205.18 |
| 4,201,204 | 5/1980 | Rinne et al. | 128/203.27 |
| 4,248,217 | 2/1981 | Brisson | 128/203.27 |
| 4,257,415 | 3/1981 | Rubin | 128/205.18 |
| 4,305,388 | 12/1981 | Brisson | 128/204.17 |
| 4,374,521 | 2/1983 | Nelson et al. | 128/204.26 |

*Primary Examiner*—Henry J. Recla
*Attorney, Agent, or Firm*—Richard G. Heywood

[57] ABSTRACT

A heated oxygen system for emergency core rewarming in treating victims of severe hypothermia that includes a dry oxygen source, a separate heater compartment having an inlet connected to receive oxygen from the source, first heater means for heating the oxygen in the heater compartment, a resuscitator hose and mask connected to the outlet of the heater compartment, and second heater means for maintaining a predetermined temperature of the heated oxygen delivered to the resuscitator mask, and a portable equipment case for housing the oxygen system including the power source and heater controls therefor and other emergency airway equipment and supplies.

29 Claims, 15 Drawing Figures

HEATED OXYGEN SYSTEM AND PORTABLE EQUIPMENT CASE FOR HYPOTHERMIA VICTIMS

BACKGROUND OF THE INVENTION

The invention relates generally to apparatus for the treatment of hypothermia, and more particularly to portable heated oxygen systems for administering to the profoundly hypothermic victim.

Hypothermia is one of the most frequently encountered and yet often overlooked aspects of emergency medicine. Accidental hypothermia is defined as "a condition in which the core body temperature is less than 35° C. (95° F.) as a result of accidental exposure", and is to be distinguished from intentional hypothermia deliberately induced as a medical procedure. However, hypothermia like other medical conditions is gradated by the degree of severity and the symtoms and urgency of treatment may differ radically at different levels. In mild hypothermia above 35° C. (95° F.), the accepted treatment is passive rewarming by natural or endogenous heat generation, which is simple, requires no equipment (other than a warm environment and/or blanket), and has no inherent morbidity. Moderate hypothermia occurs in the range of 32° to 35° C. (89.6° to 95° F.) and may produce loss of motor control, slurred speech and amnesia; marked hypothermia occurs at body core temperatures from 28° to 32° C. (82.4° to 89.6° F.) and is indicated by muscle rigidity, peripheral cyanosis and shock; and severe hypothermia occurs at temperatures from 25° to 28° C. (77° to 82.4° F.) at which the victim may have lost deep tendon reflexes and ventricular fibrillation and may appear dead with no palpable pulse or audible heartbeat. Body temperatures below 25° C. (77° F.) cause cardio-pulmonary arrest and death. These forms of hypothermia clearly present life-threatening medical problems complicating the treatment of the victim.

It seems surprising that the medical and paramedical fields have been slow in undertaking the intensive study of the nature and scope of cold stress, and its debilitating effect on the human body depending upon the relative severity resulting from exposure and traumatizing conditions coupled with the physical variables of individuals. Of course, the problems inherent in treating hypothermia victims are generally compounded in accidental hypothermia cases because most of these naturally occur to outdoor people, such as swimmers, campers and hikers, at remote locations in nature. In short, cold air and water exposure have been recognized for a long time as the primary potential for rapid heat loss, and various first-aid or emergency medical therapy for the profoundly hypothermic victim have been proposed.

Other than passive rewarming in the case of mild hypothermia, the traditional treatment of accidental hypothermia has been active external or peripheral warming. This involves the application of heat to the external body surface as by thermal blankets, heated bath emmersion, heat packs and the like, but most of these techniques are not available in the field at the rescue site. Furthermore, rapid external rewarming can produce various "rewarming shock" conditions that can be critical. The hypothermia victim is frequently dehydrated, the neuro-regulatory systems are functioning slowly, and the blood circulatory metabolism is not balanced. Thus, it should be recognized that "afterdrop" frequently results from external rewarming techniques in which the core temperature continues to drop (the cold at the periphery being driven inwardly) as the outer body is rewarmed. Obviously, cooling of the heart is critical since a reduced heart temperature of 28° C. (82° F.) can lead to total arrest and it is difficult to defibrillate a cold heart. In short, rapid peripheral or external rewarming of the accidental hypothermia victim may create additional hazards that become fatal and, at best, cannot be managed effectively in a non-hospital setting.

It is becoming established that the safest and most efficient technique for treating the severely hypothermic victim is by active core rewarming, i.e. the delivery of heat primarily to the body core or central circulation system (and also avoiding simultaneous rapid rewarming of the skin and extremities). The physiologic concept here is that if the heart, brain and lungs warm first, their control of perfusion, oxygenation and heat distribution will minimize core temperature afterdrop and the corporal metabolic hazards. A large number of hospital therapy techniques are available for rapid core rewarming, including heated peritoneal dialysis, heated gastric lavages, heated hemodialysis or intravenous fluids, extra corporeal circulation by femoral access (heart-lung machine) and inhalation rewarming. Only inhalation rewarming is a suitable technique for use by paramedics and other trained emergency rescue personnel at a rescue site or during transport to hospital or clinical facilities. Hayward et al U.S. Pat. No. 4,319,566 is relevant to inhalation rewarming and stresses the importance of delivering warm, water-saturated air or oxygen directly to the head, neck and thoracic core as the strategic body area to minimize "afterdrop" of core temperature without stimulating return of peripheral blood with high acidity and potassium concentration. However, while Hayward et al '566 approaches the problem of core rewarming, it teaches a steam heat generating apparatus for breathing patients only and one that is impractical at best in emergency rescue efforts in the field—the emphasis in this patent is on humidification as well as warming of air, and humidification itself creates problems systemically in a non-breathing patient as well as in the functioning of certain resuscitation equipment.

In addition to the publication literature cited in Hayward et al '566, some other reports of inhalation rewarming techniques include "Emergency Management of Accidental Hypothermia" by Rodney D. Edwards, M.D.; "Resuscitation From Hypothermia: A Literature Review", Report No. CG-D-26-79, Final Report—February 1979, by U.S. Department of Transportation (U.S. Coast Guard); "SASS Hypothermia-Cold Water Survival" (Critical Care Supplement), 1983, by David S. and Sara J. Smith. In addition to patent literature cited in Hayward et al '566 are U.S. Pat. Nos. 923,751; 946,307; 999,950 and 4,197,842.

SUMMARY OF THE INVENTION

The invention is embodied in a heating and distribution system for inhalation gases to be used in emergency resuscitation and inhalation rewarming of hypothermic victims in which the inhalation gas (i.e. oxygen) is metered from a source into a primary electrically controlled heating unit, a resuscitator hose is connected to receive heated gas from the primary unit and includes a secondary heating unit to maintain preselected temperatures at the resuscitator mask; and the invention further comprises a portable equipment casing for the heating system and other paramedical airway supplies and like emergency equipment in which the equipment casing provides electrical control features for heated field operations as well as efficient portability.

One of the principal objects of the present invention is to provide an improved heated inhalation apparatus for the emergency resuscitation of hypothermia victims, and one which is relatively lightweight and highly portable and accommodates all necessary ancillary equipment.

Another object is to provide an emergency technique and apparatus for the resuscitation of non-breathing (i.e. comatose) victims of profound hypothermia, and continued optimum breathing assistance after resuscitation.

Another object is the provision of a heated oxygen system that is simple in operation and capable of safe, efficient use by non-medical personnel.

Another object of the invention is to provide a battery-operated electrical system for efficiently operating and controlling first and second heating units for inhalation rewarming apparatus, and which is safe and rapid in operation so that emergency treatment can be quickly performed.

Another object of the present invention is to provide an improved emergency oxygen inhalation therapy for rapid core rewarming and to increase coronary arterial oxygenation to minimize or obviate ventricular fibrillation and the tendency toward anoxic pulmonary edema in hypothermia victims.

Still another object of the present invention is to provide a portable equipment case housing the heated oxygen system and efficiently providing for ancillary airway and paramedical equipment and supplies for emergency rescue operations.

A further object is to provide electrical control circuitry for operating heaters for controlled warming of oxygen supplies for inhalation rewarming, and which also controls drug warming and electronic thermometers and the like for the beneficial medical treatment of hypothermia victims and others during emergency rescue operations.

These and still other objects and advantages will become more apparent hereinafter.

DESCRIPTION OF THE DRAWINGS

In the accompanying drawings which form a part of this specification and in which like numberals refer to like parts wherever they occur.

DESCRIPTION OF THE PREFERRED EMBODIMENTS

Figures 1, 2, 3:
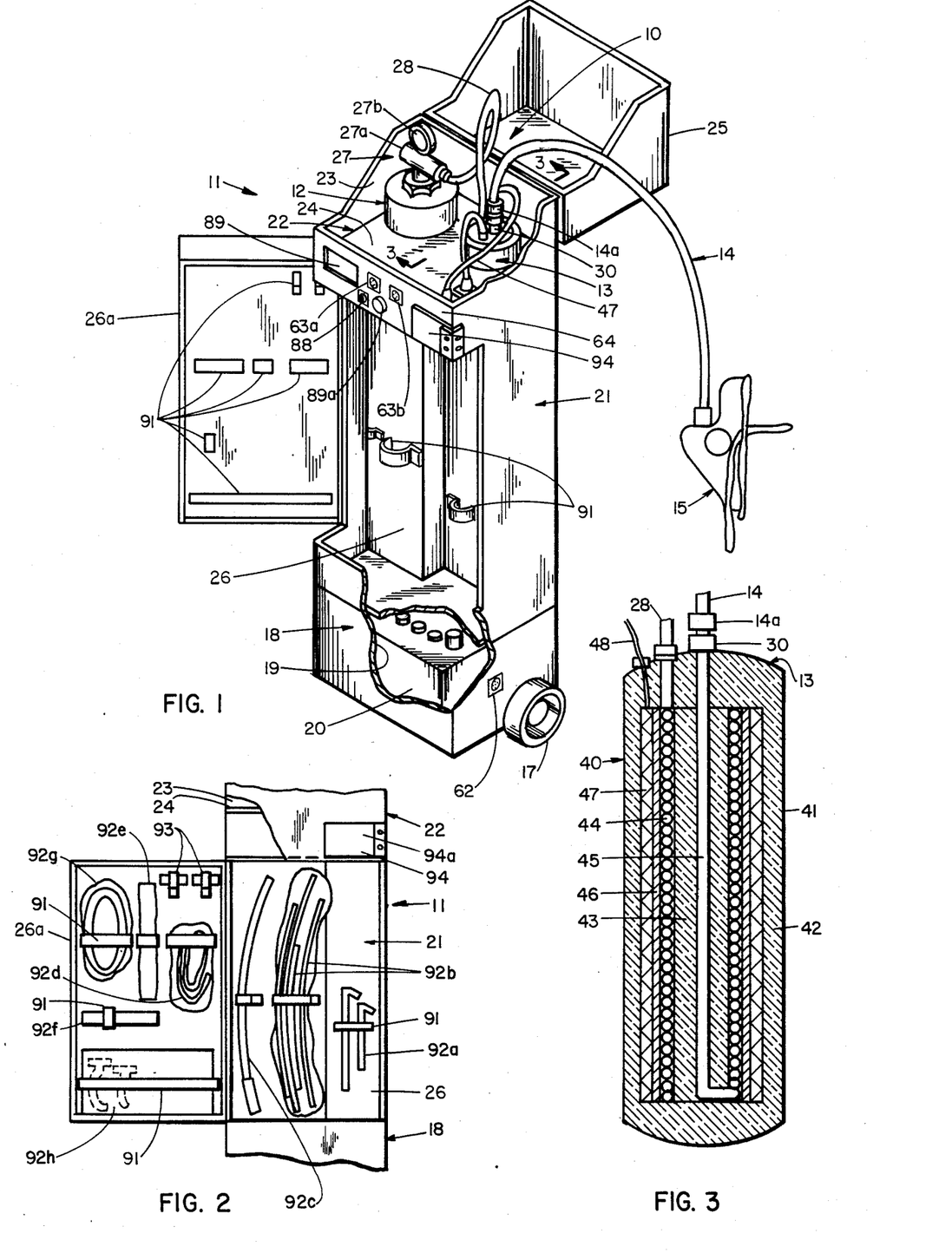
FIG. 1 is a perspective view of an oxygen heater unit and portable equipment case therefor embodying the present invention, the equipment case being open to show the control area and the storage area for paramedic equipment or the like and being partly broken away at the bottom to show an electric power source for the unit.
FIG. 2 is an enlarged fragmentary front elevational view of the opened equipment case to illustrate paramedic equipment storage therein.
FIG. 3 is a cross-sectional view of one form of oxygen heater unit taken substantially along line 3—3 of FIG. 1.
Figures 12, 13, 14, 15:
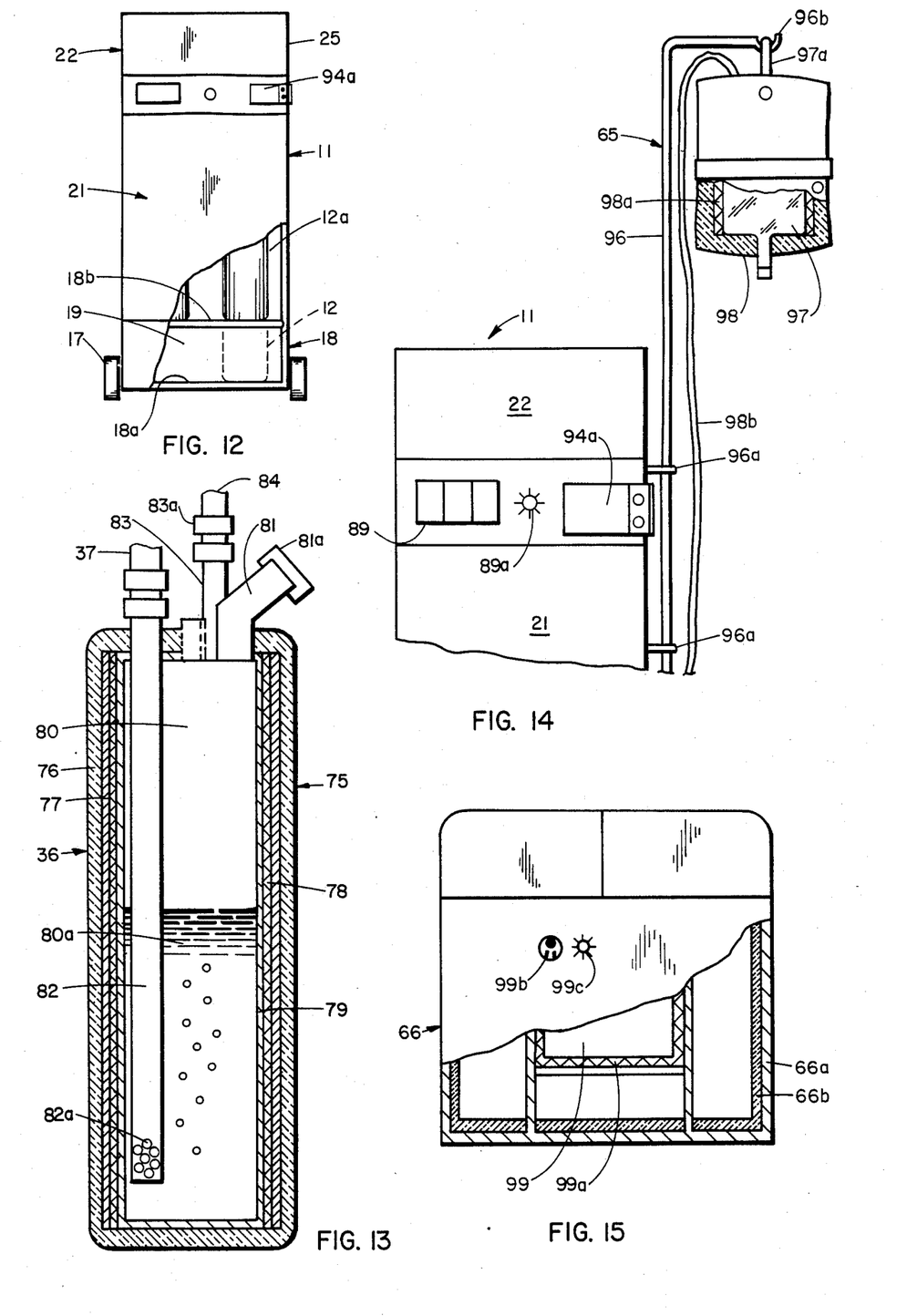
FIG. 12 is a front elevational view, partly broken away, showing an alternative oxygen tank storage arrangement in the equipment case.
FIG. 13 is a cross-sectional view of a humidifier unit for use in one embodiment of the present invention.
FIG. 14 is a front view of an equipment case showing a heated I.V. delivery system, partly broken away.
FIG. 15 is a side elevational view, partly in section, of a heated drug box forming part of this invention.

Referring now to the drawings, it will become apparent that important features of the present invention are the provision of a heated inhalation gas or oxygen system 10 (FIGS. 1 and 10) for inhalation rewarming of hypothermia victims and the provision of portability of that system and other paramedical equipment, supplies and apparatus in an equipment case 11 (FIGS. 1, 2 and 12). In addition to providing the electrical circuit and controls for operating the oxygen system heating units, the equipment case 11 also is adapted to provide for controlled heating for other emergency materials as will appear.

Figure 4:
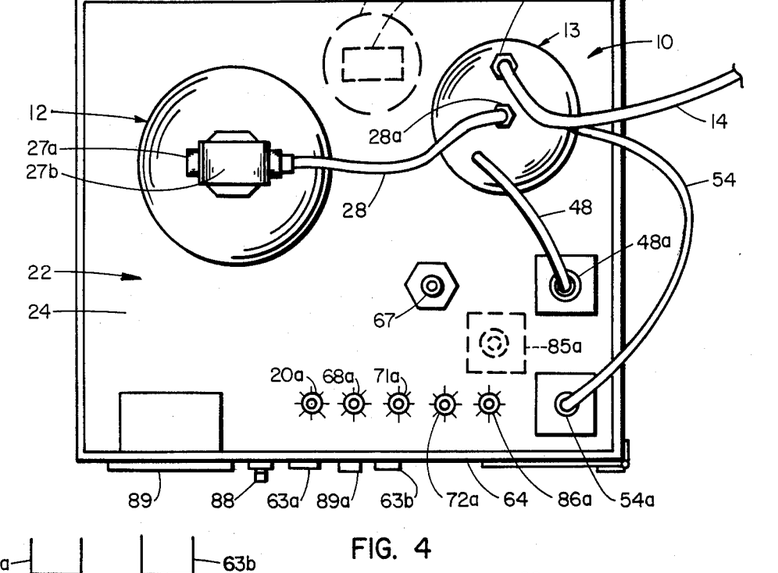
FIG. 4 is a top plan view of the top of the equipment case showing the control panel for the heater unit.
Figures 10, 11:
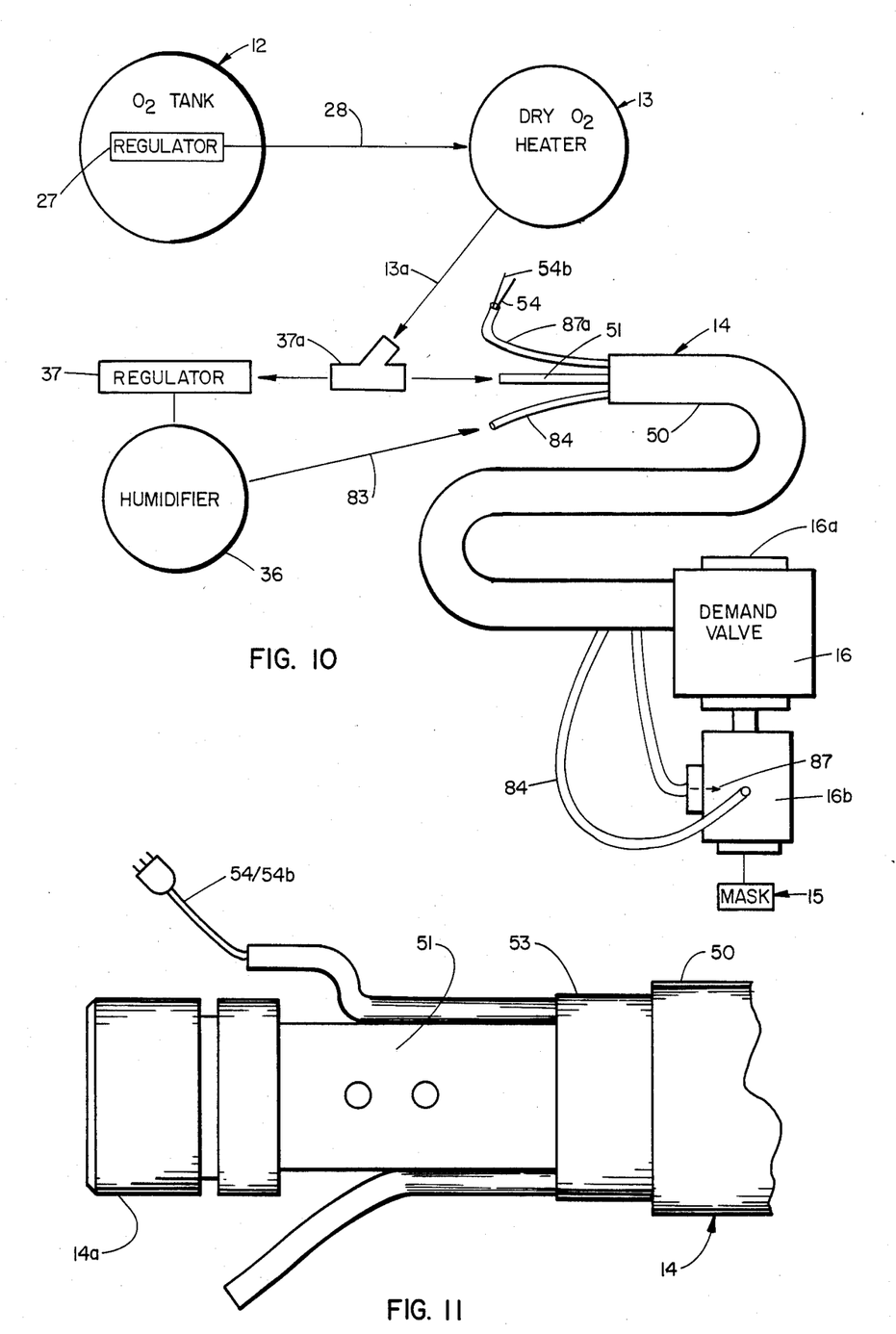
FIG. 10 is a diagrammatic view of a heated and humidified oxygen system embodying the invention.
FIG. 11 is a greatly enlarged fragmentary view showing the details of the oxygen delivery hose.

As shown in FIGS. 1, 4 and 10, a preferred inhalation gas or oxygen system 10 in its basic form includes a dry oxygen source in the form of tank 12 for compressed dry oxygen gas ($O_2$), a primary heating unit 13, a resuscitator or oxygen delivery hose 14 and mask 15 with appropriate valves and controls to be described. The portable or mobile equipment case 11 is mounted on wheels 17 for mobility and convenience in its preferred form, but the components of the invention are adaptable to a weight/mass quotient that permits other packing or encasing for relative ease of portability into remote rescue sites where the wheeled case 11 would be awkward.

Referring to FIG. 1, the case 11 includes a lower base section 18 having an interior compartment 19 adapted to house a battery 20 that functions as the electric power source for the heated oxygen system 10 and other electrical components of the present invention. The upper main body portion of the equipment case 11 has an intermediate housing section 21 hingedly connected to the base section 18 for access to the compartment 19, and an upper control section 22 forms a compartment 23 with a bottom control panel 24 and a cover member 25 is hinged to the main body portion. It is clear that the oxygen tank 12 is disposed in the intermediate section 21 with its top portion and valved regulator discharge 27 being positioned in the control section compartment 23 for ready access. The tank 12 shown in FIG. 1 is an "E" or long dry oxygen ($O_2$) tank that extends into the base section 18 and rests on the bottom wall 18a thereof, as shown in broken lines in FIG. 12. However, it will also be clear from FIG. 12 that an insert shelf 18b may be provided across the base or at the bottom of the intermediate section 21 so that the case 11 can accommodate "D" or short O₂ tanks 12a. The case 11 can house two "E" long tanks 12 or two "D" short tanks 12a or one of each, but in the preferred embodiment only one oxygen tank will be provided for the heated oxygen system 10 even though an auxiliary or standby reserve tank should be available.

Referring again particularly to FIGS. 1, 4 and 10, the heated oxygen system 10 includes one of the "E" or "D" tanks 12, 12a of compressed oxygen having its head portion located in the control section 22 of the equipment case 11. A typical O₂ tank is pressurized with oxygen to about 2500 psi and will deliver approximately 160 liters/minute outflow upon demand. The tank outlet is controlled by a typical regulator 27a to maintain a discharge gas pressure in the range of about 40–90 psi, which shows on gauge 27b. This O₂ gas discharge from the regulator is through conduit tubing 28 connected by universal quick connect couplers 28a to the inlet 29 of the primary heating unit 13. Dry oxygen gas is heated in heating unit 13, as will be described, and then flows out from outlet 30 through quick connect coupler 14a into resuscitator hose 14 (FIGS. 6, 10 and 11), and is then metered through the mask 15 to the hypothermic victim. As will be discussed more fully, the regulated heated oxygen outflow to resuscitate a non-breathing (i.e. comatose) hypothermic victim will be at a pressure of at least 40 psi in order to inflate the victim's lungs and will be delivered on manual demand at spaced breathing intervals of approximately 5 seconds in small volumetric amounts in the range of ½ to 2 liters and typically about 400 cc.

It should be understood that the basic procedure contemplated for the profoundly or severely hypothermic patient—one who is non-breathing and exhibits all of the signs of death—is the administration of straight dry oxygen heated to a temperature in the range of 37.5°–43° C. (99.5°–109.5° F.). In the past, high humidification of oxygen has been deemed critical to prevent excessive drying, but humidity creates other complications and the essential control factor in rescue work is to save the victim's life. Therefore, non-humidification with carefully monitored temperatures in the primary heater unit 13 and in a secondary heater unit 53 in the resuscitator hose 14 is believed important in initial resuscitation and inhalation rewarming. It will be understood that small amounts of moisture in the gas will be beneficial to a breathing patient, and once resuscitation has been effected, the heated oxygen can be humidified to help restore moisture to the mucous membranes and to assist thermal coloric transfer in the heating process. As shown in FIGS. 10 and 13, the apparatus of the present invention includes a humidifier unit 36 having a regulator controlled inlet 37. The regulator 37 is adjustable to control the humidified gas outflow between 1 to 20 liters/minute and when operating at about 15–20 psi will produce a metered outflow of about 1 to 2 liters of humidified oxygen that has been preheated in the heater unit 13. The humidifier unit 36 receives a portion of the heated dry oxygen through conduit 13a from the primary heater unit 13 and diverted at a T-connection 37a, and a constant flow of humidified oxygen is fed from the humidifier unit 36 for mixing with dry oxygen at the resuscitator mask 15, as will appear.

Figures 7, 8, 9:
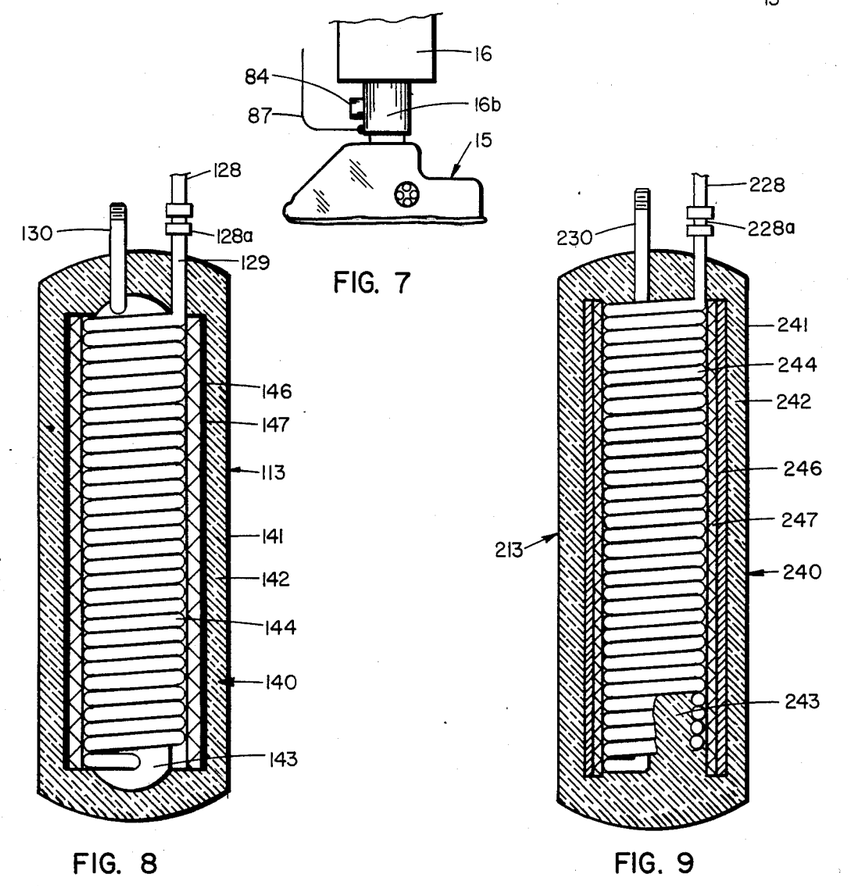
FIG. 7 is a fragmentary view of the oxygen mask and demand valve showing a temperature sensor probe for controlling oxygen delivery heating.
FIG. 8 is a cross-sectional view, similar to FIG. 3 showing another embodiment of the oxygen heater unit.
FIG. 9 is a cross-sectional view showing a further embodiment of the oxygen heater unit.

Referring to FIG. 3, one form of the primary heater unit 13 comprises a heater tank or compartment 40 having an outer shell 41 which is insulated with an insulation material 42 impervious to heat and a central core 43 of insulation material is also provided. A coil of tubing 44 is arranged helically around the central core 43 and has an inlet end connected by the coupler 28a to the delivery tube 28 from oxygen tank 12 and has an axially disposed outlet pipe or conduit 45 extending through the central core 43 and being connected at its outlet 30 to the resuscitator hose 14 by the coupler 14a. A copper sleeve 46 sheathes the helical tubing coil 44 which, in turn, is wrapped in or circumscribed by a belt heater 47 wired to the electric circuitry by lead line 48 plugged into socket 48a on the control board 24 of the casing 11. Thus, the primary heating unit 13 is controlled by the heater 47 to rapidly heat oxygen flowing through the coil 44 and through outlet tube 45 to the resuscitator hose and mask 14 and 15. Modifications of the primary heater unit 13 are shown in FIGS. 8 and 9. In FIG. 8, the primary heater unit 113 has an insulated outer shell 141 with an open or hollow central core 143. The helical coil of tubing 144 is centrally disposed and circumscribed by an annular or belt heater 147 which is encompassed by a sleeve or wrapper 146 of aluminum or other heat conductive material. The FIG. 9 embodiment shows an insulated core 243, as in FIG. 3, but the sleeve 246 of copper or like conductive material is disposed outwardly of the annular heater 247 to contain and radiate the heat inwardly to the coil 244. It should be understood that the primary heater unit 13 operates at a continuous temperature in the range of 225° to 250° F. in order to bring up the temperature of cold oxygen gas flowing therethrough to about 100° to 110° F., and proper selection of insulation and other materials is important. For instance, both styrofoam and polyethylene insulation materials will break down under the heater operation and should not be used. A medium density foam rubber such as "CHR" by General Gasket Corp. has been found satisfactory although other insulation materials may be used.

Figure 6:
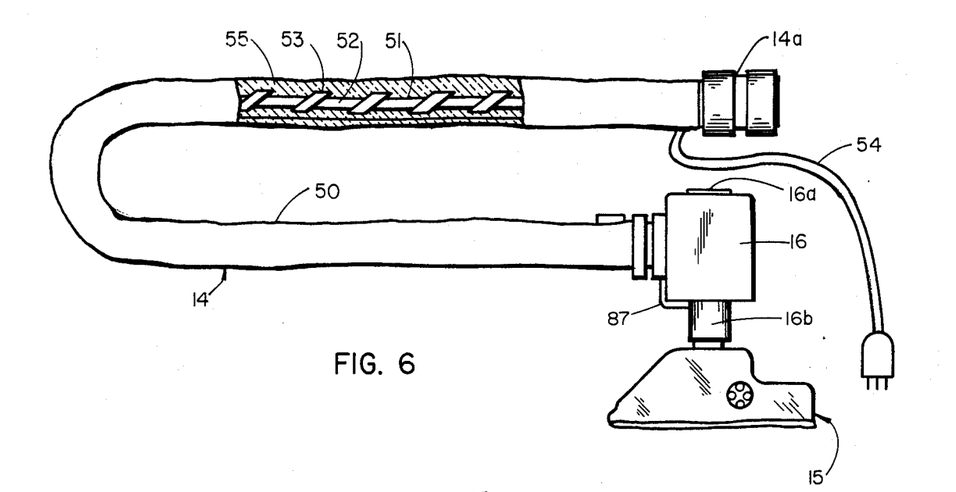
FIG. 6 is an elevational view, partly broken away, illustrating the oxygen delivery hose and mask and heating means therefor.

Referring particularly to FIG. 6, the resuscitator hose 14 in its basic form comprises an elongated flexible conduit 50 having a central tubing core 51 defining the internal oxygen passage 52 and being wrapped with a secondary belt heater unit 53 having electric lead 54 to connect to plug 54a on the control board 24 of the casing 11. The core and heater unit 51, 53 are insulated with a flexible material 55 impervious to heat. It may be noted that the quick connect coupler 14a (and other tubing couplers) are a standard universal fitting for all resuscitator tubes.

Figure 5:
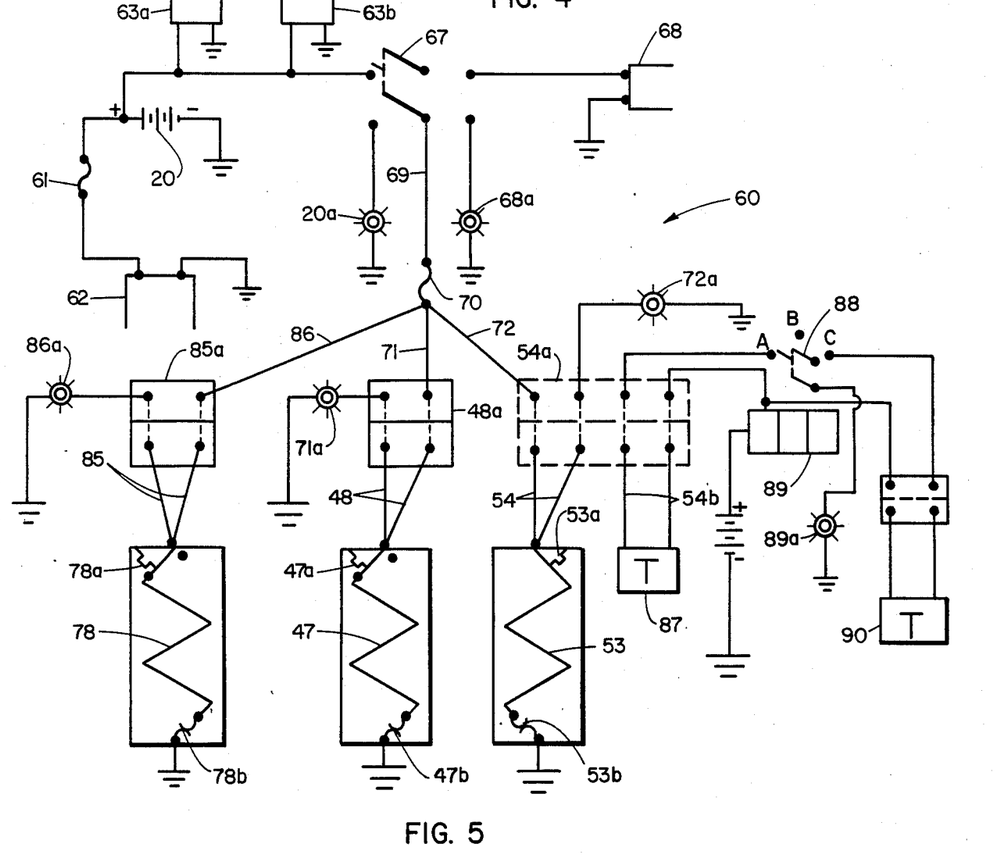
FIG. 5 is a typical wiring schematic for the heated oxygen system.

Referring to FIG. 5, the electrical control circuit 60 for operating the units of the invention comprises the 12 v. battery 20 disposed in the bottom compartment 18 of the casing 11 and forming the primary power source for the entire system. The battery 20 is grounded and connected on the positive side through an overload fuse 61 to a charging unit plug 62 located on the base section 18 and being connectable to a conventional recharging unit (not shown) of an emergency vehicle (not shown). The positive side of the battery also connects to a pair of auxiliary plugs 63a, 63b located on a front panel 64 of the control section 22 to accommodate a heated I. V. unit 65 (FIG. 14) and heated drug box 66 (FIG. 15), to be described. A main double throw toggle switch 67 connects the battery 20 to the circuit 60, or selectively to an alternate external D. C. power source 68 (such as directly from the emergency vehicle). A pair of "on" lights 20a and 68a located on the control panel 24 indicate which power source is on. The main power line 69 from the main switch 67 connects through a fuse 70 to the distribution lines for the heater units. Line 71 connects to plug 48a on the control board 24 into which the lead 48 from the primary unit heater 47 is connected, and light 71a on the control board 24 indicates an "on" condition. It should be noted that the primary heater 47 is provided with a main sensor control or thermastat 47a which operates the heater at its constant temperature of 225°–250° F. to do the primary heating of cold oxygen flowing from the tank 12, 12a through the heater unit 13. This heater 47 also has a secondary safety cutout 47b set to open at 300° F. Line 72 connects to the plug 54a on the control board 24 into which the lead 54 from the secondary heater unit 53 of the resuscitator hose 14 is connected, and light 72a indicates an "on" condition. The secondary heater unit 53 is provided with a main sensor control or thermastat 53a which operates to turn the heater unit 53 on at 100° F. and off at 110° F. responsive to the temperature of the gas at the resuscitator mask 15. A secondary safety or cutout fuse 53b is set to be on at 100° F. and off at 115° F. as a backup to the main sensor control 53a. Thus, the temperature of the delivery oxygen at the resuscitator mask 15 is carefully monitored and maintained within a 15° F. maximum range at safe optimum inhalation temperatures.

Still referring to FIG. 5 and also to FIGS. 10 and 13, the control circuit 60 is designed to accommodate another heater circuit for humidifying the portion of oxygen circulated through the humidifier 36. The humidifier 36 comprises a cylindrical tank 75 having an insulated outer shell 76 with an interior conductive copper or like metal sleeve 77 that circumscribes an annular heater 78. An inner tank or liner 79 is positioned within this outer heated casing 76, the liner 79 being formed of a heavy plastic or metal alloy of a non-corrosive, non-carcinogenic nature and defining an interior waterproof chamber 80 for distilled water 80a. The chamber 80 is filled through an opening 81 having a cap 81a. A standpipe 82 connects the outlet side of the regulator 37 and is disposed longitudinally in the chamber 80 and has outlet openings 82a through which oxygen gas is percolated through the heated water to humidify this gas, and an outlet conduit 83 is connected by a quick connect coupler 83a to a delivery conduit 84 contained within the resuscitator hose 14 in parallel by-pass relation with the dry oxygen delivery conduit 50 therein. As shown in broken lines in FIG. 4, the humidifier 36 is adapted to be positioned in the equipment case 11 and the heater 78 has electrical leads 85 that connect to another plug 85a that may be provided on the control panel 24 and is connected to the main power lead 69 by a connector 86. An "on" light 86a is also positioned on the control panel 24. It will be clear that the humidifier 36 is quickly connectable into the basic system 10 when a severely hypothermic victim has been resuscitated to a breathing condition even though the initial resuscitation and preferred core rewarming technique is to eliminate and by-pass humidification.

Still referring to FIG. 5, the control circuit 60 accommodates a digital thermometer 87 located in the mixing chamber 16b (FIG. 10) for providing a constant temperature monitor of the delivery gas at the resuscitator mask 15. The secondary hose heater 53 has leads 54 and the thermometer sensor probe 87 has leads 54b, and both leads may be wired through a separate feeder conduit 87a or the like contained in the hose unit 14 and are plugged into the control panel 24 at plug 54a. The digital thermometer unit has a three position switch 88 with position "A" connecting the constant temperature sensor 87 to the digital printout 89 on front panel 64 of the equipment case 11, as shown in FIG. 5. Position "B" is an "off" position, and position "C" permits an auxiliary thermometer probe 90 to be connected into the circuit 60 for monitoring patient core temperatures. An indicator light 89a on the front panel 64 shows an "on" condition of the switch 88 in either the "A" or "C" position, and it will be understood that the digital readout has its own internal light (not shown).

Referring again to FIGS. 1 and 2, the intermediate section 21 of the equipment case 11 houses the dry oxygen tank 12, 12a and primary heater unit 13 in the rearward portion of compartment 21a adjacent to the rear wall, and also houses the humidifier unit 36 shown in broken lines in FIG. 4 as previously set out. A stepped partition wall 26 is provided to separate this back compartment 21a from a front equipment compartment 21b for airway supplies and other emergency equipment. The front compartment 21b is closed by a door 26a, and both the door 26a and the partition wall 26 are outfitted with straps or holders 91 for the purpose of retaining the various supplies in precise locations. As shown in FIG. 2, typical airway equipment includes larynoscope blades 92a, endotracheal tubes (E.T.) 92b, esophageal obstructed airways (E.O.A.) 92c, coiled oxygen tubing (nasal) 92d, larynoscope handle 92e, syringe (E.O.A.) 92f, E.O.A. mask 92g and oral airways 92h. Spare batteries 93 may be stored, and a separate special shelf 94 closed by door 94a may be provided for juvenile-sized airway supplies or the like.

In the use of the invention it will be apparent that the equipment case 11 contains all necessary supplies and equipment for effective resuscitation as well as the entirely contained heated inhalation gas system 10. The power switch 67 will be turned on while the rescue team is enroute to the rescue site so that the primary heating unit 13 and secondary heater 53 will be at temperature and have an initial supply of heated dry oxygen ready for immediate resuscitation efforts depending upon the condition of the hypothermic victim. The basic system 10 for extreme emergency resuscitation of severe hypothermia utilizes only the dry oxygen hook-up to avoid complications with moisture interference in the inhalation gas delivery and monitoring equipment, which is controlled by the demand valve 16. As shown in FIGS. 6, 7 and 10, the demand valve 16 used in this system is of well-known configuration and of the positive-pressure type that meters inhalation gas from the resuscitation hose 14 to the mask 15 either upon manual application of the push button or trigger control means 16a in the case of a non-breathing victim or upon inhalation demand by a breathing victim. The use of dry oxygen in resuscitating a non-breathing victim prevents any increase in moisture that may contribute to pulmonary endema and thus complicate rescue operations later, and also obviates fouling of the demand valve 16 itself which won't work efficiently with moist oxygen. Thus, dry oxygen is delivered through the valve 16 upon demand by manual application of the trigger control 16a to open the internal valve mechanism (not shown) through the timed effort of the trained paramedic or upon negative inhalation pressure demand by the breathing victim. This oxygen at about 40–90 psi, in volumes of 1 to 2 liters in manual application, flows through a mixing chamber 16b to the mask 15 itself. The mixing chamber 16b primarily forms a passage of the dry oxygen, but is the point of locating the thermometer 87 and thermostatic controls 53a, 53b for regulating the heated oxygen delivery through the resuscitation hose 14, 50 so that the output or delivery temperature of oxygen at the mask 15 is closely monitored.

Referring again to FIG. 10, when the victim is breathing either at initial rescue efforts or as a result of resuscitation, the humidifier unit 36 may be quickly coupled into the system 10 to provide the advantages of humidified oxygen to the victim. The humidifier heater 78 can be provided with an independent on-off switch (not shown) in lead 86 or preferably is "on" and in "ready" condition when the main circuit 60 is switched on. The heater 78 rapidly heats distilled water 80a in the chamber 80 to saturate the upper chamber atmosphere and oxygen gas is also percolated through this hot water to bring the gas to a predetermined saturated condition. As indicated, only a portion of the total heated dry oxygen from primary heater unit 13 is diverted through the humidifier unit 36 for humidification and the remainder of the dry oxygen gas is delivered through tee 37a and the main gas conduit 51 in the resuscitator hose 14, 50 to the demand valve 16 and this dry gas flow is controlled by the demand valve 16, as stated. The flow of the humidified portion of oxygen is controlled by regulator 37, and is delivered through ancillary by-pass conduit 84 directly to the mixing chamber 16b and in by-pass relation to the demand valve 16 whereby the internal valve mechanism is not affected by this humid gas which is aspirated into and mixed with dry oxygen in the mixing chamber 16b during flow to the mask 15.

The heater system 60 of the present invention includes provision for integrating ancillary heated equipment beneficial to the treatment of hypothermia victims including the heated I.V. warming unit 65 (FIG. 14) and the heated drug box 66 (FIG. 15). As shown in FIG. 14, the equipment case 11 may be adapted with mounting or support brackets 96a for an I.V. hanger pole 96, and an I.V. bottle 97 with hanging loop 97a is suspended from hook 96b in a typical manner. The I.V. bottle 97 is encased in a heated insulated container 98 having a belt heater 98a to heat the I.V. bottle and fluid contents for delivering warmed fluid to the victim, as needed. Obviously, the heated I.V. solution becomes immediately systemic and contributes to rapid core rewarming. The heater 98a is connected by leads 98b to plug into the heater circuit 60 in either of plugs 63a or 63b on the front panel 64 of the equipment case 11 or, as shown, may be plugged into the plug 62 in the bottom section 18. Similarly, the heated drug box 66 comprises a drug case having an outer housing or shell 66a with an insulation lining 66b. An interior compartment 99 of the case 66 has a heater 99a therein for heating preselected drugs to be administered to hypothermic victims at rescue sites. Internally administered drugs are frequently needed by both breathing and unconscious victims, and both heated injected and orally administered drugs will facilitate the raising of body temperatures and be beneficial. The heater 99a has a plug connection 99b located on the outer housing 66a for connection to the plug 63a or 63b on the emergency case front panel 63, and an "on" light is provided on the drug box 66 to show when the heater 99a is operating.

From the foregoing it will be apparent that a novel heated oxygen system and equipment case is provided for the treatment of hypothermia victims to meet the objectives of the present invention. The invention is only limited by the scope of the claims appended hereto.

What is claimed is:

1. Emergency medical apparatus adapted for use in the emergency inhalation treatment of hypothermia victims, comprising a pressurized source of dry inhalation gas for resuscitation administration and core rewarming; a gas delivery system including a resuscitator hose having one end connected to said source and an opposite end, demand valve means connected to the opposite end of said resuscitator hose, a mask connected to said demand valve means whereby dry inhalation gas is metered to said mask; an electrical heater system including a power source and electrical control circuit means connected to said power source, primary heater means connected to said electrical control circuit for heating inhalation gas delivered through said resuscitator hose to a predetermined temperature, said electrical control circuit means including temperature control means connected to said primary heater means for regulating the temperature of said primary heater means; a humidifier unit connected upstream of said resuscitator hose to receive a portion of dry inhalation gas for selectively humidifying said portion of said dry inhalation gas outflow from said primary heater means, a mixing chamber located between said mask and demand valve means for receiving the dry inhalation gas metered from said resuscitator hose through said demand valve means, and means for delivering said portion of humidified inhalation gas from said humidifier unit to said mixing chamber in parallel by-pass relation with the remainder of said dry inhalation gas metered thereto from said demand valve means.

2. The emergency medical apparatus according to claim 1, in which said primary heater means comprises a gas heating chamber for receiving dry inhalation gas from said pressurized source and including first heating means therefor.

3. The emergency medical apparatus according to claim 2, in which said primary heater means comprises an insulated tank internally containing said gas heating chamber and having a coiled tubing therein for flowing inhalation gas through said chamber in a circuitous path, and said first heating means being in heat exchange relation with said coiled tubing.

4. The emergency medical apparatus according to claim 3, in which said first heater means circumscribes said coiled tubing, and said primary heater means also includes sleeve means of heat exchange material in circumscribing relation with one of said coiled tubing and first heating means.

5. The emergency medical apparatus according to claim 4, in which said sleeve means is positioned between said coiled tubing and said first heating means and is in heat exchange relation with both.

6. The emergency medical apparatus according to claim 4, in which said sleeve means is positioned in circumscribing relation with both of said coiled tubing and first heating means.

7. The emergency medical apparatus according to claim 2, in which said primary heater means further comprises second heater means in heat exchange relation with said resuscitator hose for maintaining a controlled temperature of the dry inhalation gas flowing from said gas heating chamber through said resuscitator hose to said mask.

8. The emergency medical equipment according to claim 7, in which said temperature control means operates said second heater means of said primary heater means and is disposed upstream of said mask for regulating the temperature of heated gas passing through said resuscitator hose.

9. The emergency medical apparatus according to claim 8, in which said temperature control means comprises a main thermostatic temperature sensor for operating said second heater means at a constant temperature in the range of 100°–110° F., and a secondary thermostatic temperature sensor having a safety cutout for disconnecting said second heater means from said electric control circuit at a temperature of about 115° F.

10. The emergency medical apparatus according to claim 2, in which said source of dry inhalation gas comprises a tank of compressed dry oxygen having an outflow pressure regulator discharging such dry oxygen at a pressure in the range of 40–90 psi, and said primary heater means including a first thermostatic control means for operating said first heater means at a constant temperature in the range of 225°–250° F., and second thermostatic control means having a safety cutout for disconnecting said first heater means from said electrical control circuit at a temperature of about 300° F.

11. The emergency medical equipment according to claim 1, including means for selectively dividing dry inhalation gas outflow from said pressurized source and delivering a portion thereof to said humidifier unit for humidification and directly delivering the rest of said divided dry inhalation gas directly to said demand valve means through said resuscitator hose, and the outflow of humidified inhalation gas from said humidifier unit being connected to said mixing chamber in by-pass relation with said demand valve means.

12. The emergency medical apparatus according to claim 11, in which said resuscitator hose comprises a flexible insulated casing having a main conduit for the passage of dry inhalation gas from said pressurized source to said demand valve means, said primary heating means comprising first heater means in heat exchange contact with said main conduit, and a secondary conduit between said humidifier unit and said mixing chamber for the passage of humidified inhalation gas therebetween in by-pass relation with said main conduit and said demand valve means.

13. The emergency medical apparatus according to claim 1, in which said electrical control circuit includes a control panel having a digital readout, and a digital thermometer sensor for constantly monitoring heated gas temperatures of said mixing chamber.

14. The emergency medical apparatus according to claim 13, which includes an auxiliary thermometer probe adapted to be connected in the electrical control circuit for selectively monitoring core temperatures of hypothermia victims.

15. The emergency medical apparatus according to claim 1, in which said humidifier unit includes an insulated container having an internal fluid heating compartment having a fill spout, means for regulating the flow of said portion of oxygen gas to said internal compartment and percolating said gas through the fluid therein, and fluid heating means in heat exchange relation with the fluid contents of said chamber.

16. The emergency medical apparatus according to claim 1, which comprises a portable equipment case for said apparatus which includes a main storage section having a first compartment adapted to house a tank of compressed oxygen gas as said pressurized source of dry inhalation gas, said resuscitator hose and mask and primary heater means therefor, and said humidifier unit, and which further includes a second compartment in said equipment case for the storage of said equipment and supplies.

17. The emergency apparatus according to claim 16, in which said second compartment includes door means and interior wall means accessible therethrough, and said wall means being provided with multiple holder means constructed and arranged for removably mounting emergency airway equipment and like medical supplies in predetermined locations for optimum orderly availability for use.

18. The emrgency medical apparatus according to claim 17, including a separate ancillary compartment adapted for housing relatively small supplies and special equipment, said ancillary compartment being accessible through second door means on said equipment case.

19. The emergency medical apparatus according to claim 1, in which said primary heater means comprises first heater means in heat exchange relation with said resuscitator hose for controlling the temperature of dry inhalation gas flowing therethrough, said temperature control means controlling said first heater means and being located upstream of said mask for regulating the temeprature of heated gas delivered to said mask.

20. The emergency medical apparatus according to claim 19, in which said temperature control means comprises a main thermostatic temperature sensor for operating said first heater means for said resuscitator hose at a constant temperature in the range of 100°–110° F., and a secondary thermostatic temperature sensor having a safety cutout for disconnecting said first heater means from said electric circuit at a temperature of about 115° F.

21. The emergency medical apparatus according to claim 1 in which said resuscitator hose includes a primary gas passageway connected between said pressurized source of dry inhalation gas and said demand valve means for delivering the entire supply of heated dry inhalation gas to said mask for forced resuscitation of a non-breathing victim by manual operation of said demand valve means.

22. The emergency medical apparatus according to claim 21 in which said resuscitator hose includes an additional gas passageway connected between said humidifier unit and said mixing chamber in by-pass relation with said primary gas passageway for delivering said humidified portion of inhalation gas for mixing with the dry portion of inhalation gas in said mixing chamber for normal resuscitation of a breathing victim by demand operation of said demand valve means.

23. Emergency medical apparatus adapted for use in the emergency inhalation treatment of hypothermia victims, comprising a pressurized source of dry inhalation gas for resuscitation administration and core rewarming; a gas delivery system including a resuscitator hose having one end connected to said source and a mask connected to the opposite end of said hose, and demand valve means interposed between said resuscitator hose and mask for metering dry inhalation gas to said mask; an electrical heater system including a power source and electrical control circuit, means connected to said power source primary heater means connected to said electrical control circuit for heating inhalation gas delivered through said resuscitator hose to a predetermined temperature, said electrical control circuit means including temperature control means connected to said primary heater means for regulating the temperature of said primary heater means; and including an insulated I.V. holder for an I.V. bottle, secondary heater means in said insulated I.V. holder for heating I.V. fluids in the I.V. bottle to a predetermined temperature prior to administration, said electrical control circuit including temperature control means connected to said secondary heater means for regulating the temperature thereof.

24. The emergency medical apparatus according to claim 23, in which said insulated I.V. holder comprises an insulated casing having an internal compartment to receive and hold said I.V. bottle, and said secondary heater means forms at least a partial liner for said internal compartment for heat exchange contact with the I.V. bottle.

25. Emergency medical apparatus adapted for use in the emergency inhalation treatment of hypothermia victims, comprising a pressurized source of dry inhalation gas for resuscitation administration and core rewarming; a gas delivery system including a resuscitator hose having one end connected to said source and a mask connected to the opposite end of said hose, and demand valve means interposed between said resuscitator hose and mask for metering dry inhalation gas to said mask; an electrical heater system including a power source and electrical control circuit means connected to said power source, primary heater means connected to said electrical control circuit for heating inhalation gas delivered through said resuscitation hose to a predetermined temperature, said electrical control circuit means including temperature control means connected to said primary heater means for regulating the temperature of said primary heater means; and including an insulated drug compartment for containing emergency, secondary heater means in said insulated drug compartment for maintaining the emergency drugs therein at a predetermined temperature, said electrical control circuit including temperature control means connected to said secondary heater means for regulating the temperature thereof.

26. The emergency medical apparatus according to claim 25, in which said insulated drug compartment is contained in a drug box having insulated walls surrounding said compartment, and said secondary heater means is constructed and arranged for directly heating said compartment and the emergency drugs contained therein.

27. A heated inhalation gas system adapted for emergency core rewarming in treating victims of hypothermia, comprising a source of compressed dry oxygen gas, a separate heater compartment means having an inlet connected to receive oxygen gas from said source and an outlet, said heater compartment means adapted to heat said dry oxygen gas and maintain the dry state of said oxygen gas, a resuscitator hose having one end connected to said outlet and a mask connected to the opposite end thereof for delivering heated dry oxygen gas therethrough to a hypothermia victim, an electrical control circuit including first heater means in said compartment therein for heating dry oxygen gas and second heater means in said resuscitator hose for maintaining predetermined gas temperatures therein, demand valve means located between said resuscitator hose and mask for metering heated dry oxygen gas to said mask, and temperature control means connected to said second heater means and responsive to the temperature of the gas at said mask for regulating the operation of said second heater means.

28. The inhalation gas system according to claim 27, which includes a gas mixing chamber disposed between said demand valve and said mask, a humidifier unit selectively connected to the outlet of said heater compartment and having regulator means for diverting a portion of the heated dry oxygen gas outflow from the compartment through said humidifier unit for effecting a saturated condition of said oxygen gas portion, and means for delivering said humidified oxygen gas from said humidifier unit into said gas mixing chamber in by-pass relation to the rest of said heated dry oxygen gas delivered thereto through said demand valve means.

29. The inhalation gas system according to claim 28, including other heating means for said humidifier unit.

* * * * *

UNITED STATES PATENT OFFICE
CERTIFICATE OF CORRECTION

Patent No. 4,621,633                     Dated  November 11, 1986

Inventor(s) Bowles et al

It is certified that error appears in the above-identified patent and that said Letters Patent are hereby corrected as shown below:

Column 10, (claim 1), line 24, after "gas" insert
    --outflow from said pressurized source and
    having means--; line 26, cancel "outflow from
    said primary heater means".

Column 11, (claim 13), line 51, "of" should be --at--.

Column 12, (claim 18), line 15, "emrgency" should
    be --emergency--.

Column 12, (claim 23), line 64, cancel the comma;
    line 65, after "source" insert a comma.

Column 13, (claim 25), line 36, after "emergency"
    and before the comma insert --drugs--.

Column 14, (claim 27), line 19, cancel "therein"
    and substitute --means--; same line, after
    "gas" insert --therein--.

Signed and Sealed this

Twenty-fourth Day of February, 1987

*Attest:*

DONALD J. QUIGG

*Attesting Officer*         *Commissioner of Patents and Trademarks*